Figure 1:
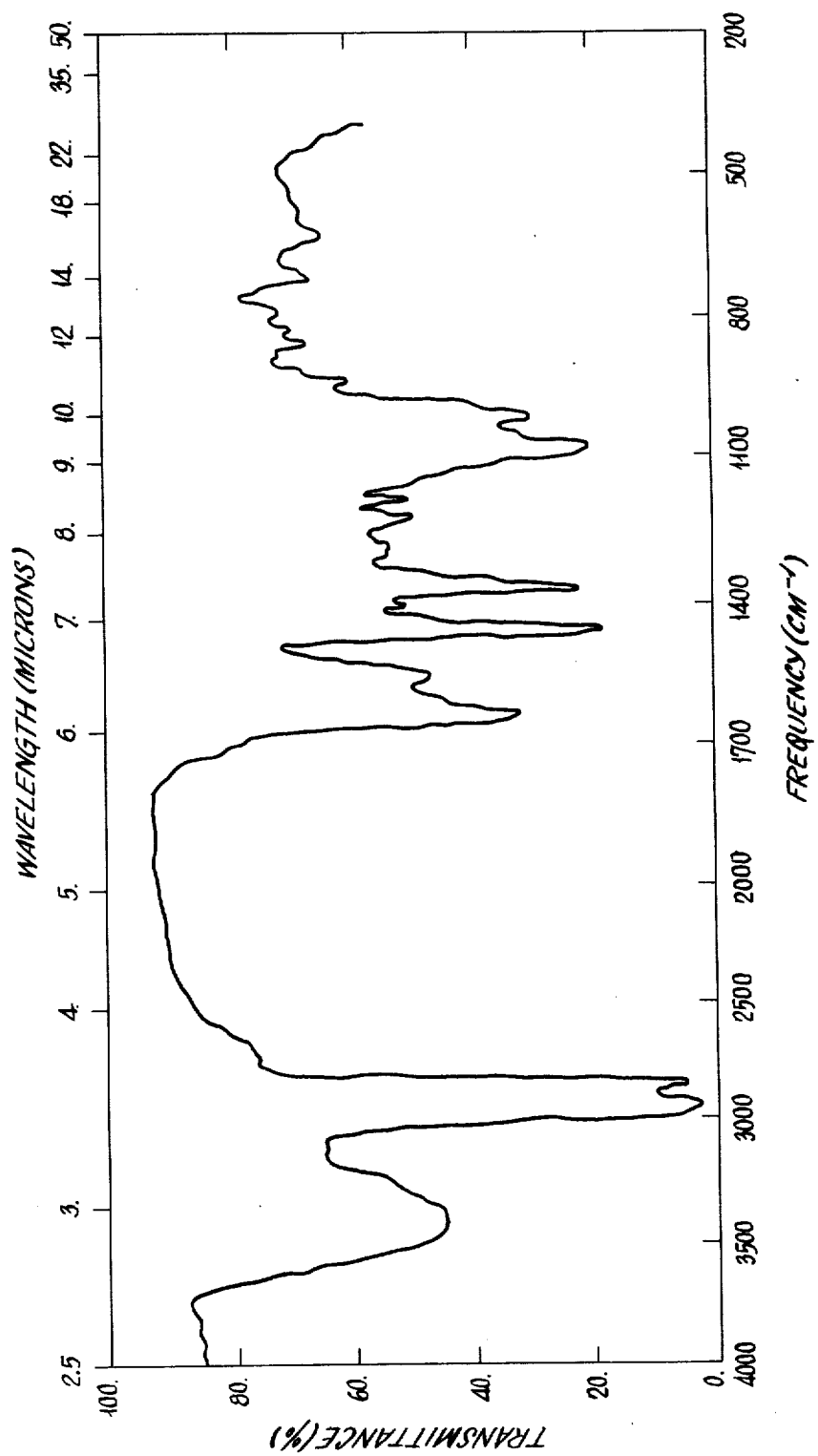

United States Patent [19]

Maiese et al.

[11] 4,024,251
[45] May 17, 1977

[54] ANTIBIOTIC FR-02A AND THERAPEUTIC COMPOSITIONS THEREOF

[75] Inventors: William M. Maiese, Bridgewater; Richard G. Wax, Matawan, both of N.J.

[73] Assignee: Merck & Co., Inc., Rahway, N.J.

[22] Filed: Feb. 12, 1976

[21] Appl. No.: 657,512

Related U.S. Application Data

[63] Continuation-in-part of Ser. No. 496,957, Aug. 13, 1974, abandoned.

[52] U.S. Cl. .................. 424/181; 195/80 R; 536/4; 536/17
[51] Int. Cl.² ............... A61K 31/71; C07H 3/06
[58] Field of Search .............. 536/17, 4; 424/181

[56] References Cited

OTHER PUBLICATIONS

Vos et al., "Tetrahedron Letter," 52, pp. 5173–5176, 1973.
Maehr et al., "Jour. Amer. Chem. Soc.", 95, 8449–8450, 1973.

*Primary Examiner*—Johnnie R. Brown
*Attorney, Agent, or Firm*—Richard A. Thompson; Walter Patton; Julian S. Levitt

[57] ABSTRACT

This invention relates to a new antibiotic agent which also possesses growth promoting activity. The antibiotic is isolated from the fermentation broth of *Streptomyces lactamdurans* by solvent extraction and designated Efrotomycin.

8 Claims, 2 Drawing Figures

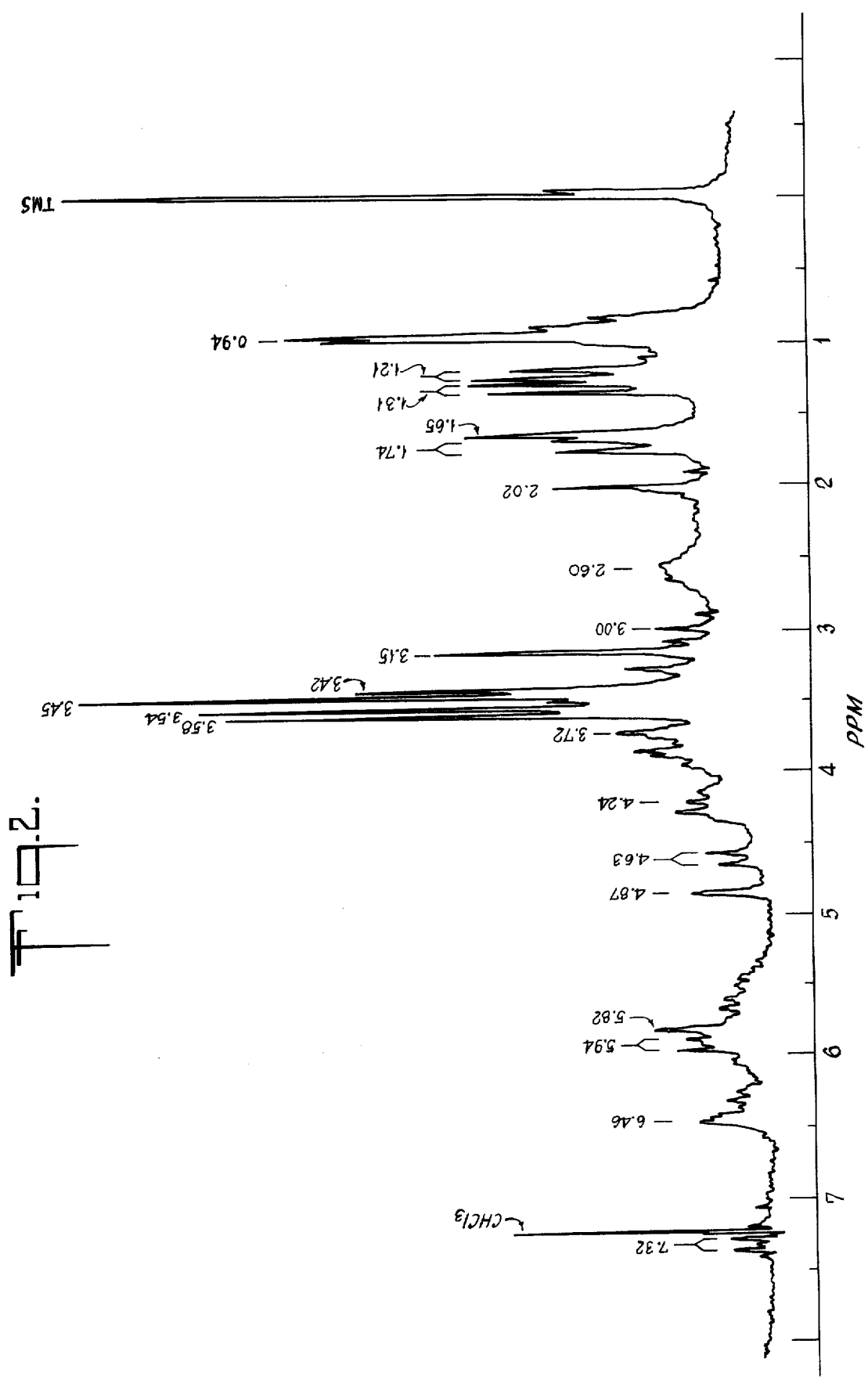

ANTIBIOTIC FR-02A AND THERAPEUTIC COMPOSITIONS THEREOF

This application is a continuation-in-part of our co-pending application Ser. No. 496,457 filed Aug. 13, 1974, and now abondoned which was a co-pending application of Ser. No. 436,425 filed Jan. 25, 1974, now abandoned, which was a co-pending application of Ser. No. 410,067 filed Oct. 26, 1973, now abandoned.

This invention relates to a new antibiotic agent which also possesses growth promoting activity, isolated from the fermentation broth of *Streptomyces lactamdurans* by solvent extraction, and designated FR-02A. The antibiotic is also designated efrotomycin.

FR-02A is an antibiotic which is effective against both gram-positive and gram-negative bacteria, and accordingly may be used in the treatment of a broad spectrum of infections in animals. More particularly, FR-02A is effective against PPLO in chickens, pigs and cattle. It is effective against mouse coccidiosis and the most prevalent types of chicken coccidiosis. It is efficacious subcutaneously against *M. galisepticum* air sacculitis in broilers, and orally effective in mice in systemic infections produced by *Bordetella bronchiseptica*. Furthermore, FR-02A can be used as a growth promoting agent for animals such as chickens, pigs and cattle.

This invention relates to the novel production by fermentation and isolation of a useful antibiotic substance that heretofore has not been reported in the prior art. More particularly, this invention relates to the preparation of antibiotic FR-02A by fermenting *Streptomyces lactamdurans* under controlled conditions, followed by isolation of said hitherto undescribed antibiotic designated FR-02A......

The antibiotic FR-02A is obtained by growing under controlled conditions the previously known microorganism, *Streptomyces lactamdurans*, in a fermentation broth and extracting the whole broth with a water immiscible polar organic solvent to obtain the antibiotic. The fermentation may be carried out in media containing suspended nutrient matter or predominantly clear media wherein the media is substantially free of suspended nutrient matter.

In the case wherein the fermentation is carried out in media containing suspended nutrient matter the antibiotic is found both in the solids comprising the mycelia and suspended nutrient matter and in the broth. The antibiotic is isolated from the solids by separating the solids from the fermentation broth by filtration, centrifugation or other suitable means and extracting the cake comprising the solids with an organic solvent, preferably a polar organic solvent. The antibiotic remaining in the broth is isolated from the broth, from which the solids have been previously separated, by extraction with a water immiscible polar organic solvent. It will be appreciated that upon delayed harventing the total level of solids in the fermentation broth will be reduced and a smaller proportion of the antibiotic will be found in the solids recovered from the broth.

In media containing no suspended nutrient matter, most of the FR-02A is found in the predominantly clear fermentation broth. In such cases the whole broth is extracted with a water immiscible polar organic solvent such as chloroform to obtain the antibiotic. Alternatively any solids, such as mycelia, may be separated from the broth prior to extracting the broth with an immiscible polar organic solvent. Furthermore, to obtain any residual FR-02A, the mycelium separated from the broth is extracted with a suitable polar organic solvent to obtain the antibiotic FR-02A.

A preferred method for obtaining the antibiotic of this invention is by growing, under controlled conditions, the previously known microorganism, *Streptomyces lactamdurans* in a medium containing suspended nutrient matter or in a clear medium substantially free of suspended nutrient matter and extracting the whole broth with a water immiscible polar organic solvent. The extraction is carried out by adjusting the pH of the broth to acid pH and adding the solvent to the broth. After mixing, the solids are separated from the broth. The broth is allowed to stand until the solvent layer separates. The solvent layer is drawn off, washed with water, dried with a suitable drying agent and evaporated in vacuo. The residue is washed with a non-polar organic solvent such as petroleum ether or hexane and air dried to yield the antibiotic FR-02A.

The further preferred method for obtaining the antibiotic FR-02A is by growing, under controlled conditions, the previously known microorganism, *Streptomyces lactamdurans* in a medium containing suspended nutrient matter. The fermentation broth is filtered to recover the solids comprising mycelium and suspended nutrient matter. After blowing the filtered cake comprising the slids as dry as possible the cake is stirred in a polar organic solvent and filtered again. After the cake has been washed with additional solvent, the combined solvent extract and wash are vacuum evaporated to leave an aqueous slurry. The pH is made acidic. The aqueous slurry is washed with a non-polar organic solvent such as petroleum ether, hexane and the like until the washings are colorless. The aqueous slurry is reextracted with a polar organic solvent. The solvent extract is dried, filtered, and evaporated in vacuo to yield the antibiotic FR-02A. For example, in accordance with the process of the invention, antibiotic FR-02A may be obtained in from about 40–50 percent pure form.

Alternatively, the fermentation may be carried out in a medium substantially free of suspended nutrient matter. The fermentation broth is filtered to recover the mycelium. The mycelium is extracted with a polar organic solvent. The extract is dried and evaporated to dryness in vacuo. The residue is shaken with a non-polar organic solvent such as petroleum ether, hexane and the like. The organic solvent is decanted after centrifugation to sediment the residue. The residue is air-dried to obtain antibiotic FR-02A.

A still further preferred method of obtaining the antibiotic of this invention is by growing, under controlled conditions, the microorganism, *Streptomyces lactamdurans*, in a fermentation broth and extracting the broth after separating the solids comprising mycelium or mycelium and suspended nutrient matter. The pH of the fermentation broth is made acid and the solids comprising mycelium or mycelium and suspended nutrient matter is separated. The fermentation broth free of solids is mixed with a water immiscible polar organic solvent. After mixing, the layers are allowed to separate. The organic layer is drawn off, dried with a suitable drying agent, and evaporated to dryness in vacuo. The residue is washed with a non-polar organic solvent such as petroleum ether or hexane and air dried to obtain antibotic FR-02A.

In the processes described above wherein extractions are carried out with water immiscible polar organic solvents, representative examples of said solvents include alkyl esters of lower alkanoic acids such as methyl formate, ethyl formate, methyl acetate, ethyl acetate, n-butyl acetate, isobutyl acetate, ethyl propionate; a ketone such as cyclohexanone; or a halogenated lower hydrocarbon such as chloroform, methylene chloride, carbon tetrachloride, ethylene dichloride, 1-chloro-2,2-dimethylpropane, tetrachloroethylene, or bromoform.

In the processes ddescribed above wherein extractions are carried out with polar organic solvents, representative examples of said solvents include lower alkyl esters of lower alkanoic acids such as methyl formate, ethyl formate, methyl acetate, ethyl acetate, n-butyl acetate, isobutyl acetate, ethyl propionate; a ketone such as acetone, methyl ethyl ketone, or cyclohexanone; or a halogenated lower hydrocarbon such as chloroform, methylene chloride, carbon tetrachloride, ethylene dichloride, 1-chloro-2,2-dimethylpropane, tetrachloroethylene, or bromo-form.

In addition to the production of FR-02A, it has been reported in the literature that *S. lactamdurans* NRRL 3802 elaborates the antibiotic Cephamycin C (*Antimicrobial Agents and Chemotherapy*, Sept. 1972, p. 122–131, Vol. 2, No. 3, "Cephamycins, a New Family of β-Lactam Antibiotics" and Belgian Pat. No. 764,160). As a consequence of FR-02A being highly soluble in water-immiscible organic solvents whereas Cephamycin C is virtually insoluble in water immiscible organic solvents, the two materials are readily separated from each other. Accordingly, extraction of the broth with a water immiscible solvent permits each antibiotic to be obtained in a form free of contamination by the other.

The antibiotic FR-02A isolated from the fermentation broth is subjected to further purification by chromatography through molecular sieve followed by chromatorgraphy over a surface active adsorbing agent. A suitable molecular sieve is a cross-linked dextran such as the molecular sieve known by the Pharmacia Fine Chemicals Inc. trade name Sephadex LH-20. FR-02A may be eluted by a lower alkanol such as methanol. A suitable surface active adsorbing agent is a hydrophobic non-ionic macro porous copolymer of polystyrene cross-linked with divinylbenzene known by the Rohm and Haas trade names Amberlite XAD-1 to XAD-12. A preferred resin for purifying FR-02A is XAD-2. Suitable solvents for eluting adsorbed FR-02A are aqueous solutions of lower alkanols e.g. aqueous solutions of methanol, ethanol, isorpopanol, butanol and the like. The preferred solvent for eluting FR-02A from XAD-2 resin is 50% isopropanol-water.

The organism which produces FR-02A is a previously known strain of *Streptomyces lactamdurans* designated as MA-2908 in the culture collection of Merck & Co., Inc., Rahway, New Jersey. It was isolated from a soil sample and has been placed on permanent deposit without restrictions as to availability with the culture collection of the Northern Utilization Research and Development Division, Agricultural Research Service, U.S. Department of Agriculture (formerly Northern Regional Research Laboratories), Peoria, Illinois 61604 and is available to the public under culture No. NRRL 3802.

Complete taxonomy and morphology studies of *Streptomyces lactamdurans* are reported in Belgian Pat. No. 764,160. Based on taxonomic studies *Streptomyces lactamdurans* was identified as a new actinomycete. It was found to belong to the genus *Streptomyces* and it possesses many attributes of the known species *Streptomyces fradiae*. Biochemically the two are almost a perfect match but morphologically there are important differences. For example, the aerial mycelium of *S. fradiae* is seashell pink as compared to the cream color of *S. lactamdurans*. On the basis of this difference and other characteristics the microorganism was assigned the species name *Streptomyces lactamdurans*.

*Streptomyces lactamdurans* is simply illustrative of the type of strain of microorganism which can be used in the production of FR-02A and it should be understood that the present invention is not limited to organisms meeting these particular descriptions. This invention includes the use of the other microorganisms, including strains of actinomycetes either isolated from nature or obtained by mutation as, for example, those obtained by natural selection or those produced by mutating agents, for example, X-ray irradiation, ultraviolet irradiation, nitrogen mustards and the like which, under suitable conditions will yield FR-02A.

FR-02A is produced during the aerobic fermentation of suitable aqueous nutrient media under controlled conditions via the inoculaton with the organism *Streptomyces lactamdurans*. Aqueous media, such as those employed for the production of other antibiotics are suitable for producing the antibiotic FR-02A. Such media contain sources of carbon, nitrogen and inorganic salts assimilable by the microorganism. The choice of media is not critical and the fermentation may be carried out in media containing suspended nutrient matter or predominantly clear media wherein the media is substantially free of suspended nutrient matter.

In general, carbohydrates such as sugars, for example dextrose, glucose, arabinose, maltose, raffinose, xylose, mannitol and the like and starches such as grains, for example, oats, rye, corn starch, corn meal and the like can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, nutrient broth, yeast extract, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.2% to 6% by weight of the aqueous medium.

Media described in the Examples are merely illustrative of the wide variety of media which may be employed, and are not intended to be limitative.

The fermentation is carried out at temperatures ranging from about 20° C. to 37° C.; however, for optimum results it is preferable to conduct the fermentation at temperatures of from about 24° C. to 32° C. The pH of the nutrient media suitable for growing the *Streptomyces lactamdurans* culture and producing the antibiotic FR-02A should be in the range of from about 6.0 to 8.0.

A small scale fermentation of the antibiotic is conveniently carried out by inoculating a suitable nutrient medium with the antibiotic-producing culture and, after transfer to a production medium, permitting the fermentation to proceed at a constant temperature of about 28° C. on a shaker for several days. At the end of the incubation period the mycelium and the suspended nutrient matter can be recovered by centrifugation or filtration and extracted with solvent, or the whole broth can be extracted with chloroform or other water immiscible solvents or alternatively the broth may be extracted after separating the solids comprising mycelium or mycelium and suspended nutrient matter.

The small scale fermentation is conducted in a sterilized flask via a one, tw, three or four stage seed development. The nutrient medium for the seed stage may be any suitable combination of carbon and nitrogen sources. The seed flask is shaken in a constant temperature chamber at about 28° C. for a period of from one to two days and some of the resulting growth is used to inoculate either a second stage seed or the production medium. Intermediate stage seed flasks, when used, are developed in essentially the same manner; that is, part of the contents of the flask are used to inoculate the production medium. The inoculated flasks are shaken at a constant temperature for several days and at the end of the incubation period the antibiotic FR-02A is isolated at already described.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterlized medium is inoculated with a previously grown seed of the producing culture, and the fermentation is permitted to proceed for a period of several days as, for example, from 2 to 4 days while agitating and/or aerating the nutrient medium and maintaining the temperature at about 28° C. the yield of FR-02A is generally between 20 mg. to 200 mg. per liter of production broth as determined by bioassay.

ASSAY Procedure

Assays were run by the disc-plate procedure using ⅜ inch filter paper discs. The assay plates were prepared using Difco nutrient agar plus 2.0 g./l. Difco yeast extract at 10 ml. per plate. An overnight growth of the assay organism, *Vibrio percolans* American Type Culture Collection (ATCC 8461) in nutrient broth plus 0.2% yeast extract was diluted in sterile saline solution to a suspension having 40% transmittance at a wave length of 660 m$\mu$. This suspension was added at 20 ml./liter of medium prior to pouring the plates.

The assay plates were held at 4° C. until used (5 day maximum). Following the application of the antibiotic-saturated assay discs the plates were incubated at 28° C. for a period of from 16 to 24 hours. Zones of inbibition were read as mm. diameter. They were used to determine relative potencies or, when compared with a purified reference standard, the potency in $\mu$g./ml. Assays of FR-02A in fermentation broths, mycelia and suspended nutrient matter separated from fermentation broths and in broths free of solids were performed after extracting the FR-02A into a suitable solvent. Assays on solutions containing FR-02A, 200 $\mu$g./ml. using ⅜ inch discs showed 16 mm. zones of inhibition. When such an assay is performed in a quantitative fashion, from 50 to 100 $\mu$g./ml. of antibiotic can be detected.

FR-02A shows activity against gram-negative and gram-positive bacteria, coccidia and species of *Mycoplasma*. In vitro, FR-02A is effective against *E. acerplasma, Bordetella, Streptococcus faecalis, Streptococcus vulina, Streptococcus faecum, Streptococcus agalactiae, Streptococcus pyogenes, Proteus vulgaris, M. hyorhinis, M. synoviae, M. arthritidis, M. gallisepticum* and species of Pasteurella. Activity was also found against *Vibrio percolans* (ATCC 8461), *Salmonella gallinarum* (MB 1287), *E. coli* (MB 1418), *Klebsiella pneumoniae* (MB 1264), *Pseudomonas stutzeri* (MB 1231) and (MB 2765), *Bacillus subtilis* (MB 964) and (MB 797), *Staphylococcus aureus* (MB 108), (MB 210) and (MB 703), and *Psuedomonas aeruginosa* (MB 3210).

FR-02A is useful both as an antibiotic and as a growth promoting agent in animals.

When FR-02A is used as an antibiotic, the specific means employed for administering it to the animal is not critical and any of the methods now used or available for treating infected animals or animals susceptible to infection are satisfactory.

FR-02A can be used as an antibiotic, for example, in the form of pharmaceutical preparations which contain it in admixture or conjunction with an organic or inorganic, solid or liquid pharmaceutical excipient suitable for enteral, parenteral or local administration. Suitable excipients are substances that do not react with the antibiotic, for example, water, gelatin, lactose, starches, stearyl alcohol, magnesium stearate, talcum, vegetable oils, benzyl alcohols, gums, propyleneglycol, polyalkyleneglycols, white petroleum jelly, cholesterol or other known medicinal excipients. The pharmaceutical preparations may be, for example, tablets, dragees, ointments, creams or capsules, or in liquid form solutions, suspensions or emulsions. They may be sterilized and/or contain assistants, such as preserving, stabilizing, wetting or emulsifying agents; solution promoters, salts for regulating the osmotic pressure or buffers.

Where it is desired to administer the antibiotic in dry, solid unit dosage form, capsules, boluses or tablets containing the desired amount of antibiotic are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of FR-02A depending upon factors such as the type of host animal to be treated, the severity and type of infection and the weight of the host. The antibiotic may be administered on a daily basis at from about 5 to 100 mg. per kilograms of body weight.

Included in this invention are the non-toxic, pharmaceutically acceptable salts of FR-02A, for example, the alkali and alkaline earth metal salts such as those derived from sodium, potassium, ammonium and calcium or salts with organic bases, for example, triethylamine, N-ethylpiperidine, dibenzylethylenediamine.

In addition to its use as an antibiotic, FR-02A is useful as a feed additive to promote the growth of animals such as chickens, sheep and cattle. The use of FR-02A shortens the time required for bringing animals up to marketable weight.

When FR-02A is used as a growth promoter in animals, it can be administered as a component of the feed of the animals or may be dissolved or suspended in the drinking water.

When FR-02A is used as a component of animal feed, it is first formulated as a feed supplement. In such feed supplements, FR-02A is present in relatively concentrated amounts intimately dispersed in an inert carrier or diluent. The feed supplement can be added directly to the feed or made into a premix by an intermediate dilution or blending step. By inert carrier is meant one that will not react with the antibiotic and one that may be administered safely to animals. Preferably, the carrier is one that is, or may be, an ingredient of the animal ration. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The antibiotic is intimately dispersed throughout the carrier by methods such as grinding, stirring, milling or tumbling. Compositions containing from about 5 to 50% by weight of the antibiotic are particularly suitable as feed supplements.

Examples of typical feed supplements containing FR-02A dispersed in a solid carrier are:

|     |                        | lbs. |
| --- | ---------------------- | ---- |
| (A) | FR-02A                 | 5    |
|     | Wheat Standard Middling | 95   |
| (B) | FR-02A                 | 50   |
|     | Corn distiller's grains | 50   |

These and similar feed supplements are prepared by uniformly mixing the antibiotic with the carrier.

The feed supplement can be added directly to the feed or made into a premix by an intermediate dilution or blending step with an orally ingestable carrier. Compositions containing 0.03% to 5% by weight of the antibiotic are particularly suitable as premixes. These premixes are prepared by uniformly mixing the antibiotic with an orally ingestable carrier.

Such supplements or premixes are added to the animal feed in an amount to give the finished feed the concentration of FR-02A desired for growth promotion. In chickens, FR-02A is fed at a final concentration of between 50 gm. to 300 gm. per ton of feed in order to achieve the desired growth promoting result. In the case of swine, including swine infected with M. hyorhinis, FR-02A may be administered in the feed at similar levels.

In the above discussion of this invention, emphasis has been placed on solid compositions wherein the FR-02A is mixed with an edible carrier in a feed supplement, in a so-called premix or in the final feedstuff. This is the preferred method of administering the FR-02A. An alternate method is to dissolve or suspend the FR-02A in the drinking water of the animals. The quantity that may be suspended in the water without undue settling is limited. Emulsifiers or surface-active agents may be employed for this latter purpose.

It will likewise be understood by those skilled in this art that special feed supplement formulations and finished animal feeds containing FR-02A may also include vitamins, other antibiotics and growth-promoting agents and other nutritional substances.

FR-02A is useful against poultry PPLO at a range of 5 to 100 mg./kg. A preferred range for a single dose is from 35 to 45 mg./kg. For reasons of convenience a preferred method of administering the antibiotic in the treatment of PPLO is to admix the FR-02A with the animal feed. A preferred range for PPLO is from 0.0055% to 0.02% by weight of feed.

In the treatment of air sacculitis in broilers the $ED_{50}$ is 40 to 100 mg./kg. Accordingly, a useful dosage of FR-02A may vary from 10 to 150 mg./kg.

A solution or suspension for subcutaneous injection for treatment of air sacculitis in broilers may be prepared as follows:

Subcutaneous Solution or Suspension Containing 20 mg. of FR-02A Ampoule:

| FR-02A                              | 20 mg. |
| ----------------------------------- | ------ |
| Diluent: Sterile water for injection | 2 cc.  |

In the treatment of coccidiosis the preferred method of administering FR-02A is in the feed at a level of from about 0.5 to 2% by weight of feed.

It will be appreciated that the dosage to be administered depends to a large extent upon the condition and weight of the host; the parenteral route is preferred for air sacculitis and the oral route is preferred for PPLO and coccidiosis. The preferred route of administrating FR-02A for growth promotion is by admixing in feed.

The examples which follow illustrate methods by which the product of this invention may be obtained. The claimed process is capable of wide variation and modification and, therefore, any minor departure therefrom or extension thereof is considered as being within the skill of the artisan and as falling within the scope of this invention.

EXAMPLE 1

Production of Antibiotic FR-02A by Shake Flask Fermentation of *Streptomyces lactamdurans*

A lyophilized culture of *Streptomyces lactamdurans*, designated MA-2908 is used as inoculum.

The lyophilized culture is opened into a 250 ml. three-baffled Erlenmeyer flask containing 40 ml. of First Stage Seed Medium:

| First Stage Seed Medium |    |
| ----------------------- | -- |
| Primary yeast           | 1% |
| in distilled water      |    |
| pH adjusted to 7.0 with NaOH |  |

The first stage seed flask, and the subsequent second stage and production flasks, are incubated at 28° C. on a rotary shaker operating at 220 rpm.

After two days in first stage medium, one ml. from the first stage seed flask is inoculated into 40 ml. of Second Stage Seed Medium in a 250 ml. three-baffled Erlenmeyer flask.

| Second Stage Seed Medium |    |
| ------------------------ | -- |
| Ardamine YEP (99F)       | 1% |
| in distilled water       |    |

-continued

| Second Stage Seed Medium |
| --- |
| pH adjusted to 7.0 with NaOH |

The second stage seed flask is incubated for one day, then 1 ml. of the culture is inoculated into each of ten non-baffled 250 ml. Erlenmeyer flasks containing 40 ml. of Production Medium:

| Production Medium | |
| --- | --- |
| Primary Yeast | 1 % |
| Distiller's Solubles | 3 % |
| Glycine | 0.05% |
| L-phenylalaine | 0.3 % |
| Cornstarch | 2.0 % |
| Dimethylformamide | 1.0 % (by volume) |
| Mobil par-S defoamer in distilled water | 0.25% (by volume) |
| pH adjusted to 7.0 with NaOH | |

A sodium thiosulfate solution is prepared by dissolving 12.5 g. $Na_2S_2O_3 \cdot 5H_2O$ in 100 ml. distilled water. This solution is filter-sterilized, then 1 ml. is added to each of the 10 production flasks.

The ten flasks are incubated for 4 days at 28° C., and harvested.

Isolation of FR-02A

The pH of the 400 ml. of broth obtained above is adjusted to 5 with hydrochloric acid, and two volumes of chloroform are added to the broth. After thorough mixing the broth is filtered through a supercel pad. Sufficient water is added to speed up the filtration. The filtrate is allowed to stand until the chloroform layer separates. The chloroform layer is drawn off, washed twice with 500 ml. of water, dried over anhydrous magnesium sulfate and evaporated to dryness in vacuum. Five hundred ml. of petroleum ether is added to the solid residue and the solid is collected by filtration, washed with 50 ml. of petroleum ether and air dried to yield 144 mg. of FR-02A. The FR-02A is converted to the ammonium salt by freeze drying a solution of the FR-02A in 50 ml. water made basic to pH 10 with ammonium hydroxide. After freeze-drying, the product weighs 140 mg.

Since the FR-02A is found in association with the mycelia and suspended nutrient matter, the mycelia and suspended nutrient matter may first be filtered out of the fermentation broth and the FR-02A extracted from the filtered cake with a polar water miscible organic solvent such as acetone. This alternate method of isolating FR-02A is as follows:

Four hundred ml. of whole broth obtained from the above fermentation is filtered to recover the mycelia and suspended nutrient matter. The filtered cake is then stirred in 40 ml. of acetone for 30 minutes and filtered again. The cake is washed with 15 ml. acetone. The combined acetone extract and washings are vacuum evaporated at 30° C. to remove the acetone. The residue is taken up in 15 ml. of water. The pH is adjusted to 4.0 with hydrochloric acid.

An equal volume of hexane is added and stirred 10 minutes. After settling, the hexane is decanted and discarded. Two more extractions with equal volumes of hexane are made, the last one being colorless.

The aqueous slurry is then extracted with an equal volume of chloroform. A second extract with an equal volume is then made and combined with the first extract. The aqueous phase is discarded.

The chloroform extract is dried over anhydrous sodium sulfate, filtered, and vacuum evaporated to yield 106 mg. of FR-02A.

The molecular weight of FR-02A is determined to be about 1,000 by subjecting the material obtained from the fermentation process described above to chromatography on Sephadex LH-20. The material obtained from this treatment is rechromatographed on Amberlite XAD-2 to obtain an analytically pure sample.

Chromatography on Sephadex LH-20 Gel

A 0.5 ml. solution of methanol containing 106 mg. of FR-02A obtained from Example 1 above is charged to a 75 ml. bed (1.25 cm. dia. × 56 cm. ht.) of Sephadex LH-20 gel in methanol (Pharmacia Fine Chemicals, Inc., Piscataway, N.J.). The column is developed with methanol. The eluate stream is monitored with a Meeco differential refractometer and the record shows three mass peaks. Fractions are bioassayed at a 1–10 dilution with ½ inch dia. paper discs on agar-diffusion assay plates seeded with Vibrio percolans. Zones of inhibition are obtained corresponding to the third mass peak ($K_D = 0.3$) detected. The fractions corresponding to the third mass peak are combined and evaporated to yield 43 mg. of FR-02A.

The product when assayed in the above agar-diffusion bioassay using Vibrio percolans gives a 16 mm. zone of inhibition at a concentration of 200 µg./ml. The U.V. absorption in pH 7.0 phosphate buffer was:

max. 327 nm $E_{1cm.}^{1\%} = 216$
max. 232 nm $E_{1cm.}^{1\%} = 464$

The purification with Sephadex LH-20 gel may be omitted if the product obtained from Example 1 is dissolved in water at a pH of 9 (pH adjusted with dilute sodium hydroxide solution) and filtered to remove insoluble material and the filtrate freeze-dried.

Chromatography on Amberlite XAD-2 Resin

The 43 mg. of LH-20 product is further purified by chromatography on a 150 ml. bed (1.25 cm. dia. × 112 cm. ht.) of Amberlite XAD-2 resin (Rohm & Haas Co., Phila., Pa.) in 50% isopropanol-water. The charge was acidified to pH 2 to convert it to the free acid form before applying it on the column. The column was monitored by a Meeco differential refractometer and the record showed two mass peaks. Agar diffusion bioassays using ¼ inch. dia. discs and Vibrio percolans plates showed the mass peak centered at $K_D$ 3.5 to 4.0 to contain the antibiotic. Fractions corresponding to these $K_D$ values were combined and evaporated to dryness under vacuum. 16.4 mg. of antibiotic FR-02A was obtained. FR-02A is obtained as a a pale yellow solid, stable to normal handling, and analytically pure.

EXAMPLE 2

Production of Antibiotic FR-02A by Shake Flask Fermentation of *Streptomyces Lactamdurans*

A lyophilized culture of *Streptomyces lactamdurans*, designated MA-2908 is used as inoculum.

The lyophil is opened into a 150 ml. three-baffled Erlenmeyer flask containing 40 ml. of First Stage Seed Medium:

| First Stage Seed Medium | |
| --- | --- |
| Primary yeast in distilled water pH adjusted to 7.0 with NaOH | 1% |

The first stage seed flask, and the subsequent second stage and production flasks, are incubated at 28° C. on a rotary shaker operating at 220 rpm.

After two days in first stage medium, one ml. from the first stage seed flask is inoculated into 40 ml. of Second Stage Seed Medium in a 250 ml. three-baffled Erlenmeyer flask.

| Second Stage Seed Medium | |
| --- | --- |
| Ardamine YEP (99F) in distilled water pH adjusted to 7.0 with NaOH | 1% |

The second stage seed flask is incubated for one day, then 1 ml. of the culture is inoculated into each of ten non-baffled 250 ml. Erlenmeyer flasks containing 40 ml. of Production Medium having the following composition:

| Production Medium | |
| --- | --- |
| Corn steep liquor | 2.8% by weight |
| cerelose | 5.6% by weight |
| Proflo | 2.8% by weight |
| glycerol | 1.4% by volume |
| Dimethylformamide | 1.4% by volume |
| in tap water pH is adjusted to 7.3 with NaOH | |

One drop of P-2000 defoamer is added to each flask prior to autoclaving.

A sodium thiosulfate solution is prepared by dissolving 6.25 g. $Na_2S_2O_3 \cdot 5H_2O$ in 100 ml. distilled water. This solution is filter sterilized, then 0.5 ml. is added to each of the production flasks after autoclaving.

The ten production flasks (totaling 400 ml.) are then incubated for 5 days at 28° C. and harvested.

The ten flasks are pooled, the pH is lowered to 5.5 with hydrochloric acid, then 500 ml. of chloroform is added, and the mixture is stirred for ½ hour at room temperature. The mixture is then centrifuged to separate the phases, and the aqueous phase is discarded. The chloroform layer is dried over anhydrous magnesium sulfate and the solvent evaporated off in vacuo. The residue is shaken with 30 ml. of hexane. The The hexane is decanted off after centrifuging down the residue. Thirty ml. of water, made basic to pH 10 with ammonium hydroxide, is added to the residue to yield a slightly cloudy solution. For the purpose of bioassay the pH is then lowered to 8.3 with HCl, and diluted in pH 8.3 water for assay by disc test. The bioassay indicates that the yield in the fermentation flask was 327 micrograms of FR-02A per ml. of fermentation broth or 130 mg. total.

EXAMPLE 3

Production of Antibiotic FR-02A by Shake Flask Fermentation of *Streptomyces Lactamdurans*

A lyophilized culture of Streptomyces lactamdurans designated MA-2908 is used as inoculum.

The lyophil is opened into a 250 ml. three-baffled Erlenmeyer flask containing 40 ml. of First Stage Seed Medium:

| First Stage Seed Medium | |
| --- | --- |
| Primary yeast in distilled water pH adjusted to 7.0 with NaOH | 1% |

The first stage seed flask, and the subsequent production flasks are incubated at 28° C. on a roatary shaker operating at 220 rpm.

After two days in the first stage seed medium, one ml. from the first stage seed flask is inoculated into each of 10 non-baffled 250 ml. Erlenmeyer flasks containing 40 ml. of production medium substantially free of suspended nutrient matter and having the following composition:

| Production Medium | |
| --- | --- |
| Nutrient Broth (Difco) | 0.8% |
| Yeast extract (Difco) | 0.2% |
| Dextrose | 1.0% |
| in distilled water | |

One drop of P-2000 defoamer is added to each flask prior to autoclaving.

The ten production flasks are then incubated for five days at 28° C. and harvested.

Isolation of FR-02A

The ten production flasks (totaling 400 ml.) are pooled, the pH is lowered to 5.5 with hydrochloric acid, and the broth is filtered to remove mycelia. The clear filtrate is then mixed with 500 ml. of chloroform and stirred for one-half hour. The mixture is then centrifuged to separate the phases and the aqueous phase discarded. The chloroform layer is dried over anhydrous magnesium sulfate and evaporated to dryness in vacuo. The residue is washed with 30 ml. of hexane and air dried to obtain the antibiotic FR-02A.

EXAMPLE 4

Production of Antibiotic FR-02A by Shake Flask Fermentation of *Streptomyces Lactamdurans*

A lyophilized culture of Streptomyces lactamdurans designated MA-2908 is used as inoculum.

The lyophil is opened into a 250 ml. three-baffled Erlenmeyer flask containing 40 ml. of First Stage Seed Medium:

| First Stage Seed Medium | |
| --- | --- |
| Primary yeast in distilled water pH adjusted to 7.0 with NaOH | 1% |

The first stage seed flask, and the subsequent production flasks are incubated at 28° C. on a rotary shaker operating at 220 rpm.

After two days in the first stage seed medium, one ml. from the first stage seed flask is inoculated into each of 10 non-baffled 250 ml. Erlenmeyer flasks containing 40 ml. of production medium substantially free of suspended nutrient matter and having the following composition:

| Production Medium | |
| --- | --- |
| Nutrient Broth (Difco) | 0.8% |
| Yeast extract (Difco) | 0.2% |
| Dextrose | 1.0% |
| in distilled water | |

One drop of P-2000 defoamer is added to each flask prior to autoclaving.

The ten production flasks are then incubated for 5 days at 28° C. and harvested.

Isolation of FR-02A

The ten production flasks (totaling 400 ml.) are pooled, the pH is lowered to 5.5 with hydrochloric acid, and the mixture is filtered to recover the mycelia. The mycelia is extracted with 500 ml. of chloroform. The chloroform extract is dried over anhydrous magnesium sulfate and evaporated to dryness in vacuo. The residue is washed with 30 ml. hexane and air dried to obtain the antibiotic FR-02A.

EXAMPLE 5

Production of Antibiotic FR-02A by Shake Flask Fermentation of *Streptomyces Lactamdurans*

A lyophilized culture of *Streptomyces lactamdurans* designated MA-2908 is used as inoculum.

The lyophil is opened into a 250 ml. three-baffled Erlenmeyer flask containing 40 ml. of First Stage Seed Medium:

| First Stage Seed Medium | |
| --- | --- |
| Primary yeast | 1% |
| in distilled water | |
| pH adjusted to 7.0 with NaOH | |

The first stage seed flask, and the subsequent production flasks are incubated at 28° C. on a rotary shaker operating at 220 rpm.

After two days in the first stage seed medium, one ml. from the first stage seed flask is inoculated into each of 10 non-baffled 250 ml. Erlenmeyer flasks containing 40 ml. of Production Medium substantially free of suspended nutrient matter and having the following composition:

| Production Medium | |
| --- | --- |
| Nutrient Broth (Difco) | 0.8% |
| Yeast extract (Difco) | 0.2% |
| Dextrose | 1.0% |
| in distilled water | |

One drop of P-2000 defoamer is added to each flask prior to autoclaving.

The ten production flasks are then incubated for 5 days at 28° C. and harvested.

Isolation of FR-02A

The ten production flasks (totaling 400 ml.) are pooled, the pH is lowered to 5.5 with hydrochloric acid. Five hundred ml. of chloroform is added, and the mixture stirred for one-half hour at room temperature. The mixture is then centrifuged to separate the phases and the aqueous phase discarded. The chloroform layer is dried over anhydrous magnesium sulfate and evaporated to dryness in vacuo. The residue is washed with 30 ml. of hexane and air dried to obtain the antibiotic FR-02A.

EXAMPLE 6

Production of Antibiotic FR-02A by Shake Flask Fermentation of *Streptomyces Lactamdurans*

A lyophilized culture of *Streptomyces lactamdurans*, designated MA-2908 is used as inoculum.

The lyophil is opened into a 250 ml. three-baffled Erlenmeyer flask containing 40 ml. of First Stage Seed Medium:

| First Stage Seed Medium | |
| --- | --- |
| Primary yeast | 1% |
| in distilled water | |
| pH adjusted to 7.0 with NaOH | |

The first stage seed flask, and the subsequent second stage and production flasks, are incubated at 28° C. on a rotary shaker operating at 220 rpm.

After two days in first stage medium, one ml. from the first stage seed flask is inoculated into 40 ml. of second stage medium in a 250 ml. three-baffled Erlenmeyer flask.

| Second Stage Seed Medium | |
| --- | --- |
| Ardamine YEP (99F) | 1% |
| in distilled water | |
| pH adjusted to 7.0 with NaOH | |

The second stage seed flask is incubated for one day, then 1 ml. of the culture is inoculated into each of ten non-baffled 250 ml. Erlenmeyer flasks containing 40 ml. of Production Medium having the following composition:

| Production Medium | |
| --- | --- |
| Corn steep liquor | 2.8% by weight |
| cerelose | 5.6% by weight |
| Proflo | 2.8% by weight |
| glycerol | 1.4% by volume |
| Dimethylformamide | 1.4% by volume |
| in tap water | |
| pH is adjusted to 7.3 with NaOH | |

One drop of P-2000 defoamer is added to each flask prior to autoclaving.

A sodium thiosulfate solution is prepared by dissolving 6.25 g. $Na_2S_2O_3 \cdot 5H_2O$ in 100 ml. distilled water. This solution is filter sterilized, then 0.5 ml. is added to each of the production flasks after autoclaving.

The ten production flasks (totaling 400 ml.) are then incubated for five days at 28° C. and harvested.

Isolation of FR-02A

The ten flasks are pooled, the pH is lowered to 5.5 with hydrochloric acid, and the mycelium and suspended nutrient matter is separated from the fermentation broth by filtration. The filtrate is mixed with 500 ml. of chloroform and stirred for one-half hour. The mixture is then centrifuged to separate the phases and the aqueous phase is discarded. The chloroform layer is dried over anhydrous magnesium sulfate and the solvent evaporated off in vacuo. The residue is washed with 30 ml. hexane and air dried to obtain the antibiotic FR-02A.

Physical Properties of FR-02A

Elemental analysis of FR-02A is as follows:
C 60.98%
H 7.60%
N 2.60%

The corresponding empirical formula $C_{59}H_{90-96}N_2O_{21}$ is consistant with monohydrated FR-02A. This is in agreement with a molecular weight of about 1,168 of the sodium complex of FR-02A determined by field desorption mass spectrometry. Further mass spectroscopic study of FR-02A disclosed the molecular weight 1,144 for the uncomplexed compound corresponding to the empirical formula $C_{59}H_{88}N_2O_{20}$.

FR-02A as the ammonium salt is soluble in alcohol and chloroform. It is moderately soluble in water at pH 7.0 or higher. A U.V. spectrum of the ammonium salt in water showed:

λmax. 233 nm; $E_{1cm.}^{1\%} = 320$
λmax. 328 nm; $E_{1cm.}^{1\%} = 180$

After further purification FR-02A in the free acid form has the following U.V. spectrum in methanol — 0.05M phosphate buffer pH 6.85 (20:80):

λmax. 325 nm; $E_{1cm.}^{1\%} = 317$
λmax. 230 nm; $E_{1cm.}^{1\%} = 554$
λmax. 219 nm; $E_{1cm.}^{1\%} = 556$ Specific optical rotation of FR-02A sodium salt is $[\alpha]_D$-56.6 ± 0.5 (C=1, MeOH).

The nuclear magnetic resonance spectrum of antibiotic FR-02A set forth in FIG. 2 was obtained at 100 MHz in $CDCl_3$ as the solvent and tetramethylsilane (TMS) as the internal standard. Representative features of the spectrum were Doublets at 1.21(3H), 1.31(3H), 1.74(3H), 4.63(1H), 4.87(1H), 5.94(1H) and 7.32(1H) ppm; Overlapping signals of 4 other C-methyl groups centered at about 0.94 ppm; Singlets at 1.65(3H), 2.02(3H), 3.15(3H), 3.42(3H), 3.45(3H), 3.54(3H), and 3.58(3H) ppm.

FIG. 1 shows the infrared absorption spectrum of antibiotic FR-02A in a Nujol mull. FR-02A exhibits characteristic absorption in the infrared region of the spectrum at the following wave lengths expressed in reciprocal centimeters:

Broad Band at: 3400
Strong bands at: 1640, 1460, 1380, 1080, 1020
Prominent bands at: 1550, 1505, 1240, 1195, 940, 860, 720, 620

FR-02A was subjected to several analytical systems and the results are set forth below:

| | | |
|---|---|---|
| 1. | LH-20 column in MeOH (Charged $NH_4$ + salts) | $K_D = 0.30$ |
| 2. | XAD-2 column 50% iPrOH—$H_2O$— emergence (Charged free acids) | D.V.¹ = 3.5 to 4.0 |
| 3. | T.L.C. Silica gel $CHCl_3$—MeOH— Conc. $NH_4OH$ 80-20-1 | $R_f = 0.34$ |
| 4. | Paper chromatography isopropanol, phosphate buffer pH 6.0 (0.01 M.), 70-30 | $R_f = 0.9$ |

¹D.V. = Displacement volume, i.e., the number of bed volumes required to elute the antibiotic.

The FR-02A is a substantially pure material as judged by its being a single spot material on TLC and a single, gaussian shape profile detected by refractometer monitoring of the LH-20 and XAD-2 analytical columns.

The antibiotic FR-02A is believed to have the molecular structure as follows:

To further characterize FR-02A in vitro, activity data for it was obtained using an antibiotic spectrum profile. The test involves applications of a droplet of antibiotic of approximately 0.015 ml. on the surface of seeded complex agar plates. FR-02A was dissolved in 10% methanol which, by itself, did not produce zones of inhibition. The results are reported in Table 1 in terms of mm. of inhibition zones.

TABLE 1

Antibiotic Spectrum Profiles (ASP) of FR-02A in Agar Diffusion Tests

| Organism, MB# | Diameters (mm.) of Inhibition Zones FR-02A 1 mg./ml. |
|---|---|
| Bacillus sp. 633 | 18 |
| Proteus vulgaris 1012 | 10 |
| Pseudomonas aeruginosa 979 | 10H |
| Serratia marcescens 252 | 10H |
| Staphylococcus aureus 108 | 11 |
| Bacillus subtilis 964 | 19 |
| Sarcina lutea 1101 | 28 |
| Staphylococcus aureus 698* | 12H |
| Streptococcus faecalis 753 | 11 |
| Alcaligenes faecalis 10 | 19 |
| Brucella bronchiseptica 965 | 18 |
| Salmonella gallinarum 1287 | 13 |
| Vibrio percolans 1272 | 21 |
| Xanthomonas vesicatoria 815 | 13 |
| Escherichia coli 1418 | 15 |
| Ps. stutzeri 1231 | 10 |
| Klebsiella pneumoniae 1264 | 16 |
| Aerobacter aerogenes 835 | 13 |
| Erwinia atroseptica 1159 | 12 |
| Corynebacterium pseudodiphtheriticum 261 | 27 |
| S. aureus 3032 | 12 |
| S. aureus 2756 | 23 |
| Strep. faecium 2820 | 20 |
| Proteus vulgaris 838 | 18 |
| E. coli 60 | 10 |

TABLE 1-continued

Antibiotic Spectrum Profiles (ASP) of FR-02A in Agar Diffusion Tests

| Organism, MB## | Diameters (mm.) of Inhibition Zones FR-02A 1 mg./ml. |
|---|---|
| S. aureus (res. Erythromycin) 1909 | 16 |

H = Hazy Zone
*Resistant to streptomycin, streptothricin, neomycin, and viomycin.

Antibiotic FR-02A in vivo has a low toxicity and broad spectrum of antibacterial activity when tested in mice. As an example the results for a gram-negative bacterium and a gram-positive bacterium are presented in Table 2.

TABLE 2

In Vivo Test Results With FR-02A* in Mice

| Infection | | Therapy | | Toxicity** | |
|---|---|---|---|---|---|
| Organism | Route | Route | $ED_{50}$ | Tolerated | Toxic |
| Proteus vulgaris | IP | IP | 1.73 | 5.0 | 5.0 |
| Strep. pyogenes | IP | IP | 0.247 | 1.25 | 5.0 |

*Values in the table are expressed in mg./mouse. Both infections and therapeutic doses of FR-02A were administered intraperitoneally. FR-02A was administered at time of infection and again 6 hours later.
**Toxicity studies of FR-02A in noninfected mice indicate that two doses of 2.5 mg./mouse, 6 hours apart are tolerated; but higher doses i.e. 5 to 10 mg./mouse is toxic.

What is claimed is:

1. A compound designated FR-02A having the structure:

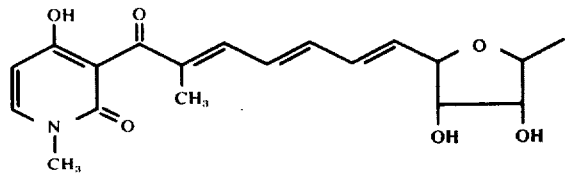

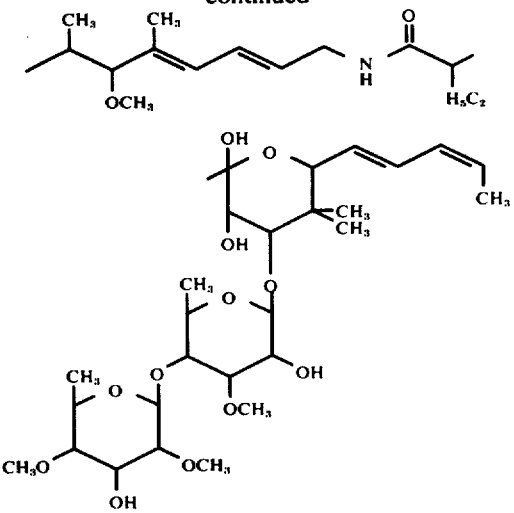

and pharmaceutically acceptable non-toxic salts thereof.

2. The compound of claim 1 in substantially pure form.

3. A composition comprising an antibacterially effective amount of FR-02A or its pharmaceutically acceptable salts and a non-toxic pharmaceutically acceptable excipient.

4. A composition for use in the growth promotion of animals comprising a growth promoting amount of FR-02A or its pharmaceutically acceptable salts and an inert carrier.

5. A composition according to claim 4 wherein FR-02A is present from 0.005 to 50% by weight.

6. A composition according to claim 4 which is a feed supplement wherein FR-02A is present from 5 to 50% by weight.

7. A composition according to claim 4 which is a premix wherein FR-02A is present from 0.03 to 5% by weight.

8. A composition according to claim 4 which is a finished feed wherein FR-02A is present from 0.005 to 0.03% by weight.

* * * * *